(12) United States Patent
Kiy et al.

(10) Patent No.: US 6,350,890 B1
(45) Date of Patent: Feb. 26, 2002

(54) METHOD FOR OBTAINING FATTY ACIDS FROM BIOMASS BY COMBINED IN/SITU EXTRACTION, REACTION AND CHROMATOGRAPHY USING COMPRESSED GASES

(75) Inventors: Thomas Kiy, Frankfurt am Main; Christoph Siffrin, Quierschied; Heinz Engelhardt, Saarbruecken; Dirk Fabritius, Frankfurt am Main, all of (DE)

(73) Assignee: AXIVA GmbH, Frankfurt am Main (DE)

( * ) Notice: Subject to any disclaimer, the term of this patent is extended or adjusted under 35 U.S.C. 154(b) by 0 days.

(21) Appl. No.: 09/744,142
(22) PCT Filed: Jul. 17, 1999
(86) PCT No.: PCT/EP99/05107
 § 371 Date: Feb. 16, 2001
 § 102(e) Date: Feb. 16, 2001
(87) PCT Pub. No.: WO00/05395
 PCT Pub. Date: Feb. 3, 2000

(30) Foreign Application Priority Data

Jul. 22, 1998 (DE) .......................... 198 32 784
Feb. 12, 1999 (DE) .......................... 199 06 474

(51) Int. Cl.$^7$ ................................................ C11C 1/00
(52) U.S. Cl. ...................................... 554/167; 554/193
(58) Field of Search ................................ 554/167, 193

(56) References Cited

U.S. PATENT DOCUMENTS 4,898,673 A   2/1990 Rice et al.

OTHER PUBLICATIONS

King, 14(10) Trends Anal. Chem. 474–481 (1995).
King et al., 344 Fresenius J. Anal. Chem. 474–478 (1992).
Cummins et al., 694 J. Chromat. B 11–19 (1997).
Wenclawiak et al., 785 J. Chromat. A 263–267 (1997).
Matsuzaki et al., 106(20) Chem. Abstr., 158274 (1987) (abstract of JP 61–261398).

*Primary Examiner*—Deborah D. Carr
(74) *Attorney, Agent, or Firm*—McKenna & Cuneo LLP (57) ABSTRACT

The invention relates to a method for obtaining fatty acid esters and fatty acids, preferably unsaturated fatty acid ethyl esters, from biological sources by continuous, combined in-situ extraction, reaction and chromatography. The invention is characterized in that simultaneously and in the same location, in the presence of a compressed gas and an 0.5–5 % stream of lower alcohols as modifiers and in the presence of an inert catalyst, the fatty acids are fully transesterified from their native fatty acid sources, which are selectively desorbed and eluated in the conditions specified above.

9 Claims, 10 Drawing Sheets

METHOD FOR OBTAINING FATTY ACIDS FROM BIOMASS BY COMBINED IN/SITU EXTRACTION, REACTION AND CHROMATOGRAPHY USING COMPRESSED GASES

This application is a 371 of PCT/EP99/05107 filed Jul. 17, 1999.

Method for the preparative-scale production of fatty acids from biomass by in-situ extraction, reaction and chromatography using compressed gases The invention relates to a method for the preparative-scale production of fatty esters—for producing fatty acids, preferably polyunsaturated fatty acids (PUFAS)—from biological sources by continuous in-situ extraction, reaction and chromatography using compressed gases.

In nature, PUFAs, in addition to oleic acid, occur in relatively high concentrations in linseed oil, hazelnut oil, poppy seed oil, hemp seed oil and fish oils. Numerous attempts have already been made to produce these valuable substances from biological sources of these types and to isolate them with a greater or lesser degree of purity. However, since the PUFAs are generally chemically bound as esters in lipids, in addition to extraction, conversion to the free acids (hydrolysis) or corresponding monoesters (transesterification) must be carried out.

Since the biological sources, in particular fish oil, are not available without restrictions, it is of interest to isolate the PUFAs from microorganisms, such as bacteria, algae etc., which have stored these fatty acids within the cells or in the cell membranes as lipids.

There is great industrial interest in industrial methods for the preparative-scale production of fatty esters, in particular of nutritionally important fatty esters, preferably polyunsaturated fatty esters. Lipids contain fatty acids, mostly bound in glycerides (mono-, di- and triglycerides), phosphatides, glycolipids and aminolipids. These bound fatty acids and free native fatty acids and their derivatives differ firstly in their frequency of occurrence in biological sources, and secondly in their activity on the human organism.

Native fatty acids and their derivatives are produced from biological sources, in addition to by classical solvent extraction of the corresponding lipids, in particular by extraction using compressed gases (for example supercritical carbon dioxide, etc.). This method termed SFE (supercritical fluid extraction), ensuring biological compatibility, is a mild much-described extraction method which is used in routine analysis and process engineering.

Extracted lipids cannot be separated directly by chromatography into the individual triglycerides, since generally a permutation of numerous naturally occurring fatty acids at the three positions of the triglyceride leads to a multiplicity of compounds which can only be separated chromatographically with difficulty.

The fatty acids are therefore extracted by means of a preceding or following reaction via cleavage of the lipids (fat cleavage) into the individual fatty acids by means of (catalytic) transesterification to form the esters of lower alcohols or by means of (catalytic) hydrolysis to give the free acids, also in the presence of a compressed gas in the reaction medium (SFR=supercritical fluid reaction).

The substances which serve as catalysts here are organic acids (formic acid, acetic acid, citric acid, etc. "Coupling chemical derivatisation reactions with supercritical fluid extraction", J. A. Fields, J. Chromatog. A, 785 (1997), pp. 239–249) and solid catalysts (e.g. Ion-exchange resins (C. Vieville, Z. Mouloungui, A. Gaset; Colloq.—Inst. Natl. Rech. Agron. (1995), 71 (Valorisations Non-Alimentaires des Grandes Productions Agricoles), 179–82; acidic aluminum oxide (B. W. Wenclawiak, M. Krappe, A. Otterbach; J. Chromatogr. A (1997), 785, 263–267)) or combinations thereof (C. Vieville, Z. Mouloungui, A. Gaset; Ind. Eng. Chem. Res. (1993), 32(9), 2065–8).

Enzymatic reactions using lipases are also known which, either in solution, or immobilized, perform the fat cleavage with subsequent extraction in the presence of supercritical gases (R. Hashizume, Y. Tanaka, H. Ooguchi, Y. Noguchi, T. Funada; JP-196722 and A. Marty, D. Combes, J. S. Condoret; Prog. Biotechnol. (1992), 8 (Biocatalysis in Nonconventional Media), 425–32).

In principle, the SFE and SFR methods can be carried out as continuous flow or batch methods. King et al. carry out extraction and transesterification in the presence of compressed gases as a batch method (J. W. King, J. E. France, J. M. Snyder; Fresenius J. Anal. Chem. (1992), 344, 474–478). In this case, firstly, extraction of lipids from a biological source takes place (here seed grains), with subsequent transesterification on the catalyst to form methyl esters. The aluminum oxide catalyst is physisorbed with ethanol. However, a disadvantage is the complex use of the samples on the catalyst, as a result of which reaction only takes place at the catalyst/sample interface. This is inadequate in the context of a preparative reaction.

King et al. describe a virtually quantitative conversion (>98%) of triglycerides to the methyl esters on immobilized lipase which is carried out as a continuous flow method. In this case corn oil and, as modifier, methanol are pumped to the carbon dioxide. This is also carried out for consistent biological sources such as soybean flakes (M. A. Jackson, J. W. King; J. Am. Oil. Chem. Soc. (1996), 73(3), 353–6).

However, the use of lipases in the continuous flow method has the disadvantage of conversion rates which are low with time.

All of the procedures described in the prior art have the disadvantage that they exhibit a spatial separation between extraction and reaction and thus do not comply with in situ preconditions and therefore do not achieve quantitative conversion. (Cf. also in the case of an esterification JP 61261398, JP 07062385 A2 and in the case of a hydrolysis K. Fujita, M. Himi; Nippon Kagaku Kaishi (1995), (1)). In addition, in the prior art, there is no advantageous inexpensive combination of reaction, extraction and chromatography.

The object of the present invention is to provide a method for the preparative production of unsaturated and saturated fatty esters and their selective isolation from biological sources.

The object is achieved by a method for the preparation and isolation of fatty esters from biological sources using continuous in-situ extraction, reaction chromatography. In the presence of a compressed gas stream and a 0.5 to 5% strength C1–C5 alcohol modifier (a) the reaction takes place on an inert catalyst in complete contact with the biological source;

(b) the reaction products are chromatographed on the inert catalyst from (a) which has chromatographic retention and exclusively desorbs and elutes the reaction products;

(c) the desorbed and eluted reaction products from (b) are extracted.

The present method has advantages compared with known procedures:

The reaction products produced are safe with regards to health and food chemistry, since 1.) ethanol is preferably used as modifier and reaction partner and
2.) solid inert aluminum oxide is used as catalyst/stationary phase and
3.) carbon dioxide is used as reaction/extraction medium and mobile phase. Neither the starting materials nor the product thus come into contact with toxic substances at any instant of the method.

Carbon dioxide serves as protecting gas atmosphere to prevent oxidations and for mild extraction and elution.

In contrast to the mentioned methods, in the present case the toxicity of the substances used is so low that these may safely be used for preparing food additives or pharmaceutical products.

The reaction products occur in pure form as solid substance or in high concentration in a suitable solvent and can readily be further processed.

In addition, the reaction products in the inventive method are selectively separated off from the starting materials, the intermediates and the byproducts.

The method can be carried out continuously. In the case of liquid starting materials, they can be fed into the flow system.

Owing to the preferred use of the inexpensive aluminum oxide as inert catalyst/stationary phase, an economically expedient, industrial preparative scale can be carried out.

The biological source can be used directly. It is not necessary to limit the amount of biomass from the biological source and the method is therefore suitable for industrial use.

The method unites and combines the process steps extraction, reaction and chromatography to form a functional unit and can therefore decrease the costs of industrial use.

By carrying out the method as a continuous flow system the desired product is constantly removed from the reaction equilibrium and permits a theoretical yield of virtually 100%. This is impossible in a batch method or via classical organic transesterification.

"In-situ extraction, reaction and chromatography" for the purposes of this invention means that the fatty esters are provided, chromatographed and extracted from the biological source in situ using compressed gases (abbreviation: SF-REC).

For this purpose a specific catalyst is required which is triturated and/or mixed in situ with the biological source, and effects the cleavage of the lipids with reaction (transesterification) with an alcohol to form the fatty ester. In addition, the inventive catalyst acts as stationary phase in which the fatty esters produced are selectively desorbed from the catalyst and are eluted in the presence of the compressed gas. Therefore, the inventive catalyst must have a chromatographic retention at which the product is not adsorbed.

The inventive parameters (conditions) are chosen so that the lipids remain on the catalyst and the fatty esters are selectively eluted. These specific parameters are explained in the examples.

The inventive method of in-situ reaction, extraction chromatography is carried out as a continuous method. Use can also be made synonymously of the term "(continuous) batch flow method". For the purposes of this invention, the term continuous method is understood as a continuous flow system in which, with progressing reaction, in the gas/modifier stream, the reaction products are chromatographed and extracted on the solid or consistent biological source in contact with the inert catalyst. A liquid biological source can be added to the gas/ethanol stream and ensures a continuous method.

The term "compressed gases" for the purposes of this invention comprises liquid, supercritical and biphasic or subcritical gases or gas mixtures. Here, those gases are expressly incorporated which are known to those skilled in the art in the sector of SFE and SFR techniques. To this extent, the compressed gas serves for extraction and is used as reaction medium. For the purposes of this invention, the gas also serves as mobile phase and is used as extraction medium. Particular preference is given to compressed carbon dioxide.

For the purposes of this invention, "modifier" means an additional stream in the presence of the compressed gas. In the context of this invention, 0.5–5% by volume of lower alcohols are used. Preference is given to an ethanol modifier of 0.5–5% by volume. Particular preference is given to 1% by volume of ethanol, preferably technical-grade ethanol. For the purposes of this invention, the modifier serves as reactant for transesterification of lipids on the inert catalyst.

For the purposes of this invention, fatty esters are obtainable from all branched and unbranched fatty acids and fatty acid derivatives, such as hydroxy fatty acids, which have a carbon chain of at least 12 carbon atoms. Preferred fatty esters are ethyl esters of fatty acids, since the alcohol required for their preparation has the lowest toxicity of the lower alcohols. The invention can be carried out for unbranched or branched C1–C5 alcohols.

Starting materials are preferably lipids from biological sources and other bound fatty acids; reaction products are fatty esters. Since, preferably, ethanol is used as reactant and modifier for the reaction (transesterification), ethyl esters of fatty acids are preferably obtained.

Obviously, free fatty acids and their salts in the biological sources are converted into their fatty esters.

In the context of this invention, complete transesterification means the conversion of all fatty acids present in the starting materials into the corresponding ethyl esters of fatty acids, with unreacted starting materials continuing to remain (adsorption) on the inert catalyst.

Inert catalyst, for the purposes of this invention, means that this catalyst in complete contact with the biological source firstly accelerates the reaction (transesterification) to the reaction products, and secondly serves as stationary phase. For this purpose the catalyst must have chromatographic retention. The catalyst may not have toxic activity on the biological source and therefore is present inert toward the reaction. Commercially conventional aluminum oxide has proved advantageous and inexpensive, which aluminum oxide in addition, can be readily mixed and/or triturated with the biological source, if appropriate together with other aids and additives (for example sea sand).

In principle, in the inventive method, any biological source can be employed and used. Obviously, biological sources are advantageous which are rich in native fatty acids as such or in the form of fatty esters, in particular lipids. If polyunsaturated fatty acids are desired, appropriate biological sources must be used. The term biological source is therefore preferably to be applied to microorganisms which can easily be cultured. In this case, preference is given to microorganisms having a high content of polyunsaturated fatty acids (PUFAs), which can readily be disintegrated. This may be chemically, enzymatically, but preferably mechanically. Particular preference is given to microorganisms having a fatty acid spectrum which predominantly comprises one or only a few bound or native fatty acids. Suitable organisms are preferably those hereinafter:

(The source used for the underlying systematics for group 1: Handbook of Protoctista, Margulis, Corliss, Melkonian, Chapman, Jones & Bartlett Publishers, Boston (1990), and for group 2: Industrial Applications of Single Cell Oils, Kyle & Ratledge, American Oil Chemist' Society, Champaign, Ill., 1992).

Figure 1:
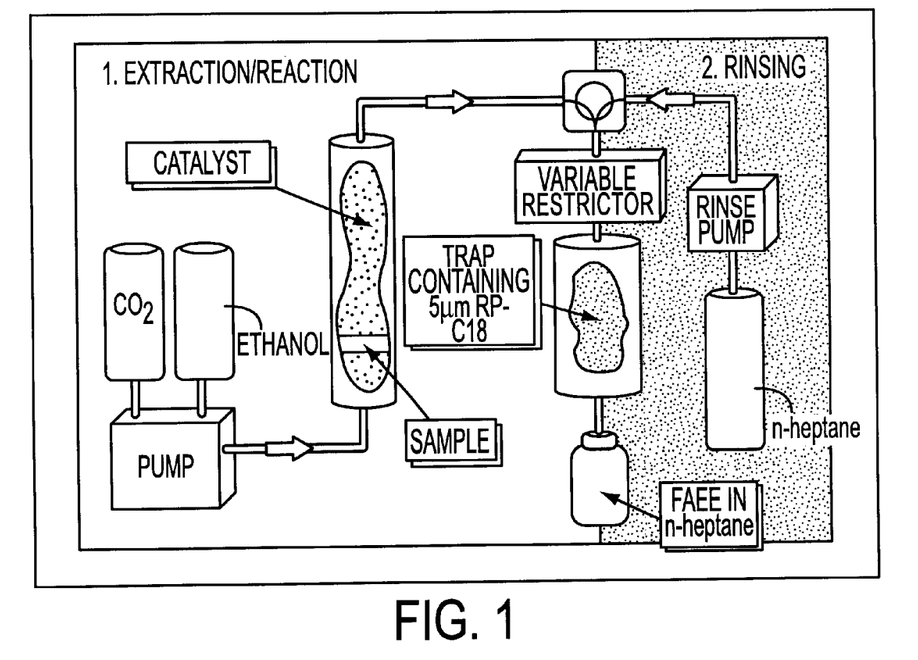

1st group: Microalgae and protozoa (=protists)
Phylum: Ciliophora
Genus: Tetrahymena, Colpidium, Parauronema, Paramecium
Phylum: Labyrinthulomycota
Genus: Ulkenia, Thraustochytrium, Schizochytrium
Phylum: Dinoflagellata
Genus: Crypthecodinium, Gymnodinium, Gonyoaulax
Phylum: Euglenida
Genus: Euglena
Phylum: Bacillariophyta
Genus: Nitzschia, Navicula, Cyclotella
2nd group: Fungi
Genus: Mortierella, Cunninghamella, Mucor, Phytium
3rd group: Bacteria
Genus: Butyrivibrio, Lactobacillus FIG. 1 describes the diagrammatic setup and arrangement of the functional units, with the terms used having the meanings specified below:

"Catalyst": Steel chamber filled with aluminum oxide. Site of the in-situ extraction, reaction chromatography.

"Restrictor": Valve or narrow capillary which resists a flowing medium and regulates the pressure system in the presence of the "$CO_2$—", "sample-", "ethanol"-pump.

Further parameters may be found in the examples.

The examples below serve for a more detailed description without restricting the invention thereto and in particular indicate the conditions under which selective extraction of the fatty esters produced can be achieved.

EXAMPLES

Example 1

General conditions:
Pressure: 70–400 bar
Flow rate: 0.5–4 ml/min
Temperature: 40–150° C.
Alcohol: 0.5% by volume to 5% by volume of ethanol
Catalysts/separation medium: 7 g of aluminum oxide A for column chromatography (ICN, acidic, activity 1), possibly other media: for example basic, neutral, coated with acids, differing particle sizes, or based on silica gel, zirconium oxide or on another basis.

Example 2

Figure 2:
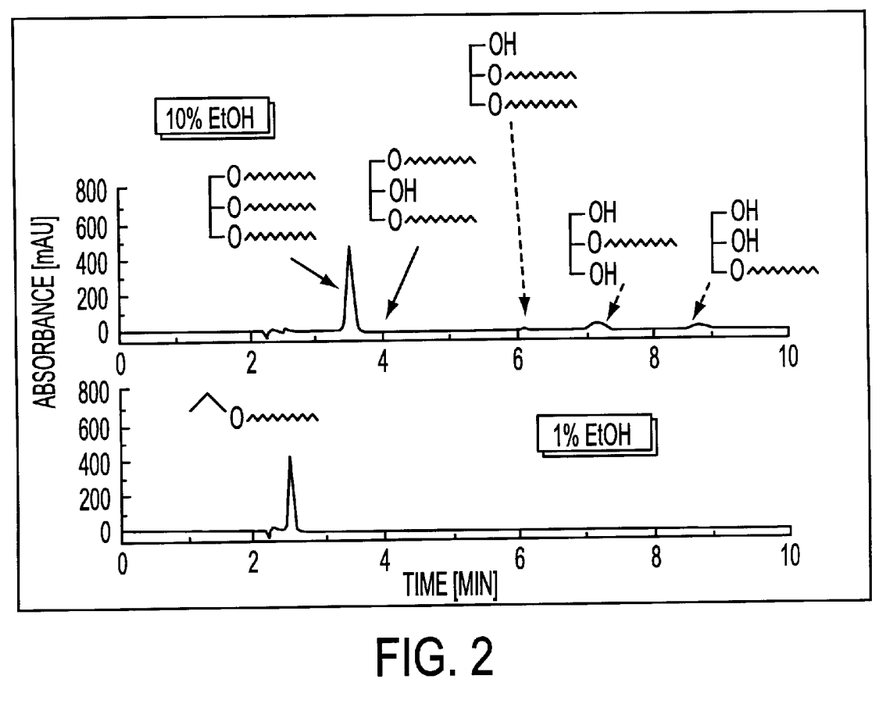

In the bottom chromatogram of FIG. 2 the analysis (on aminopropyl phase 4.6×500 mm, 10 µm; 5% ethanol as modifier, 150 bar, 40° C.) of the substances originating from the system during the process may be seen. Under the conditions given (1% EtOH) only the ethyl ester is taken off from the system. The top chromatogram shows the substances taken off from the system when 10% EtOH is fed in. Under these conditions, all substances (except for glycerol) are eluted from the system. This is equivalent to termination of the reaction. Peaks can be seen for the ethyl ester, the triglyceride and the corresponding mono- and diglycerides.

This example was carried out under the following conditions:

Instrument: HEWLETT-PACKARD SFE Module 7680T

| Sample: | Triolein (97% TLC), Fluka |
|---|---|
| Extraction chamber/reactor: | approximately 0.2 g of sample approximately 7 g of aluminum oxide A for column chromatography (ICN, acidic, activity I) |
| Conditions: | Pressure: 200 bar Flow rate: 4.0 ml/min (fluid) Modifier: 1% by volume of EtOH Temperature: 80° C. |

Trap: Trap with glass beads (0.25–0.5 mm);

Extraction time: 2 minutes static; 10 minutes dynamic; then rinsing the trap with n-heptane (about 1 ml), 8 repetitions thereof; then termination of reaction by extraction of all substances (except for glycerol) under identical conditions, but with 10% EtOH, 60 minutes.

Example 3

Analysis by SFC and GC-MS

Two techniques are used to study the course of the reaction during further optimization steps: for qualitative analysis and identification of the products, GC-MS is used. SFC serves for quantification.

A qualitative consideration of the resultant ethyl esters of fatty acids is important for determining the fatty acid spectrum, particularly for actual samples. This is studied by GC-MS. For this purpose, the esters dissolved in n-heptane are separated on a DB5 column and identified by their mass spectra. The precise chromatographic conditions are listed at an appropriate point.

Example 4

Quantitative Analysis by SFC

Quantitative analysis of the ethyl esters formed and of the unreacted triglycerides serves for determination of the yield of SF-REC. This poses the problem of being able to determine all products (ethyl esters, mono- and diglycerides; not glycerol) and the starting material (triglyceride) by one chromatographic method. Generally, in GC, only readily volatile esters (methyl esters or ethyl esters) but not the nonvolatile glycerides, can be determined directly. The glycerides must therefore first be converted into the esters of lower alcohols. In HPLC, there is the problem of UV detection. The glycerides and ethyl esters must be converted, for example, into phenacyl esters. Using SFC on amino phases and ethanol as modifier, the ethyl esters and the glycerides may be separated and detected even underivatized at 210 nm. Thus direct determination of the conversion rate is possible rapidly.

For quantification of the conversion in the model reaction (transesterification of triolein to ethyl oleate) the following method was employed:

System: HEWLETT-PACKARD SFC Chromatograph
Column: BISCHOFF AMP Prontosil-120 3 µm 200×4.6 mm
Flow rate: 3.0 ml/min
Final pressure: 150 bar
Temperature: 35° C.
Modifier: 3% ethanol
Injection: 5 µl of n-heptane solution
Detection: UV 210 nm (DAD)

The calibration lines were determined for two standards using
ethyl oleate 99% (GC) (FLUKA)
triolein 97% (TLC) (FLUKA).

Example 5

Determination of Reaction Kinetics

SF-REC was carried out on a commercial HEWLETT-PACKARD System SFE Module 7860T. To determine the reaction kinetics, the conversion rates were studied after defined time intervals: after the start of the reaction, that is to say after introducing the sample into the reaction vessel with catalyst and setting the conditions (pressure, temperature, flow rate etc.) on the instrument, the substances taken off from the reaction vessel were collected continuously over a certain period. This collection process using a trap containing a solid sorbent is carried out in two steps: the substances from the reaction chamber are extracted in what is termed a dynamic step, that is to say the extraction medium flows through the system, dissolves the sample and, after the fluid has been expanded, deposits it on the solid carrier of the trap. This is washed in a second step with a suitable solvent (here: n-heptane) and the extracted substances are transferred to a collection vessel. This washing step lasts about six minutes. During this time the flow of fluid is stopped, but pressure and temperature remain the same in the reaction chamber. The reaction proceeds further in this time. This step can therefore be described as an additional static step. To record the kinetics, after defined times, the trap is washed (see above) in order to establish how much product has formed after this time. When below the x axis of the reaction course is labeled "time [min]", this means that only the dynamic steps have been totaled. Two different reactions in which the same time sequence of steps is present are therefore comparable. Labeling the time axis with "total reaction time [min]" means that at any dynamic step, the six minutes of the static course of the reaction during the washing operation have been added. This must be taken into account when comparing the recorded kinetics.

The collection vessels (vials) are filled automatically. By weighing the vials before and after the step, the amount of n-heptane solution can be determined. For quantification, injections are made in triplicate from the respective vials for each reaction step. For the evaluation, the mean of the peak areas of the three injections is taken. From the calibration lines, the concentration and, from the amount of solution, the amount of substance are calculated. The amount of co-extracted triolein is quantified, based on the amount of triolein used. From this is calculated the theoretically achievable amount of ethyl ester (EE) of oleic acid, which corresponds to 100% reaction yield. The amount of 18:1-EE determined is based on this.

Example 6

Optimization of the Extraction/Reaction Conditions

For transesterification using SF-REC, the conditions can be varied within broad ranges. In addition to technical details such as the collection method and the "sample preparation" (for example how much catalyst per amount of sample and at which position the sample is situated in the reactor), the reaction conditions and extraction conditions such as pressure, flow rate, modifier content and temperature can be varied independently of one another. A series of parameters for optimizing the yield are thus available. Considering the apparatus set-up (FIG. 1), the individual points result therefrom as follows:

TABLE 1

| Parameter | Area | Effect on |
| --- | --- | --- |
| Collection method | Various traps:<br>- solid-phase trap (glass beads, RP material)<br>- liquid traps (collection vessel with solvent) | Product recovery |
| "Sample preparation" | - Continuous flow system: (feed of a liquid sample: sample flow rate)<br>- Batch method:<br>At which position should the sample be; how much sample per amount of catalyst; application of the sample in ethanolic solution; grinding the sample together with the catalyst | Conversion rate/loading capacity of the catalyst |
| Type of catalyst | Aluminum oxide:<br>- acidic/neutral/basic<br>- what activity state<br>- particle size/surface area<br>- precoating the catalyst with ethanol<br>Alternative materials:<br>$SiO_2$; $TiO_2$; etc.; ion exchangers | Conversion rate/reaction rate |
| Mobile phase flow rate | Variable on the present instrument between: 0.1 and 4.0 ml/min | The higher the flow rate, the more rapidly the products are removed |
| Modifier content | 0–10% ethanol | Controlling the selectivity of the extraction between starting material and product or conversion rate |
| Temperature | Variable between 40 and 150° C. | Extraction yield (density), reaction rate |
| Pressure | Variable between 80 and 360 bar | Extraction yield (density) |

Example 7

Collection Method

The collection method used is critical for whether a virtually quantitative recovery can be achieved.

After extraction with subcritical or supercritical carbon dioxide, this medium must be expanded. The pressure drop takes place at what is termed a restrictor. There, the $CO_2$ becomes gaseous and it loses the ability to dissolve samples. These then separate out as small droplets or particles which must be collected as completely as possible. In principle, on an analytical scale two methods may be chosen: collection on a solid sorbent, or in a suitable solvent. In the first case, the gas stream is passed through a trap, a tube filled with the solid sorbent. The sample is deposited in this case on the sorbent. This can occur, firstly by purely mechanical contact, for example on glass beads (0.1–0.25 mm diameter). The trap can be cooled in order to prevent evaporation of the sample or to condense the sample, increase its viscosity or freeze it out. Care must be taken to ensure that the sample is not "blown off" in the form of droplets from the trap material by the rapid gas stream. This point becomes a problem, in particular, when a modifier is employed. This is also deposited as a liquid. Since the amount of liquid exceeds the absorption capacity of the trap, losses occur, because the sample dissolved in the modifier is "blown"

away from the trap. Therefore, when modifier is used, the trap must be heated above the boiling point of the modifier, so that this, as is the $CO_2$, is present in the gaseous state and can no longer dissolve the sample. However, at this temperature, owing to the sample volatility, losses due to evaporation can occur.

After the sample was collected on the trap, it was eluted from the solid sorbent in a rinse step using a suitable solvent (rinse solvent).

The second potential method is introducing the expanded gas, which contains entrained sample droplets or sample particles, into a suitable solvent. The sample can dissolve in the solvent in this case, if it has enough time to come into contact with it. This contact time depends on the flow velocity of the $CO_2$. The solvent is introduced into a flask and the gas stream is passed through by means of a capillary. In this method, two problems chiefly result: firstly, there is the possibility that parts of the sample are deposited on the path through the capillary downstream of the restrictor. However, this is prevented by modifier addition, since this, as liquid droplets, rinses the capillary downstream of the restrictor. Feeding the solvent directly at the restrictor also rinses the sample into the collection vessel. The second problem occurs particularly during collection over a relatively long time period owing to evaporation of the solvent introduced. Feeding the solvent at the amount per time which can also evaporate per unit time can keep the amount of solvent in the collection vessel constant, but does not prevent losses due to evaporation of the sample itself. Decreasing the collection vessel temperature counteracts this. However, the temperature cannot be decreased to the extent that blockages of the capillary due to freezing out of the $CO_2$ occur (for example by acetone/dry ice).

The recovery rate of 18:1-EE (ethyl oleate, the product of SF-REC with the model substance triolein) was determined under identical conditions for the varying collection methods.

For this purpose a defined amount of a standard of 18:1-EE was weighed into an extraction thimble on an inert carrier material (sea sand). The extraction was carried out under similar conditions which were also used later for SF-REC:

System: HEWLETT-PACKARD SFE Module 7680T
Pressure: 198 bar
Temperature: 90° C.
Density: 0.53 g/ml
Modifier: 1% EtOH
Flow rate: 4.0 ml/min
Extraction time: 30 minutes dynamic The trap method with solid sorbents used was, firstly, glass beads having a diameter of 0.1–0.25 mm as inert material. Secondly, an RP-C18 material (Merck) having a mean particle size of 5 μm was packed into the trap tube. In both cases, the following temperatures were set on the instrument for the restrictor (variable restrictor, nozzle) and the trap:

Nozzle temperature during extraction: 90° C.
Trap temperature during extraction: 85° C.
Nozzle temperature for the rinse step: 70° C.
Trap temperature for the rinse step: 60° C.
Rinse solvent: 1 ml of n-heptane Thus in the trap the temperature exceeds the boiling point of the modifier ethanol (78.3° C.), so that no losses of the 18:1-EE occur in the condensed ethanol. After the extraction, the sample is rinsed from the trap with one milliliter of n-heptane.

If the two recovery rates are then compared, it is observed that only 13% of 18:1-EE was retained on the glass beads. The remainder has either been "blown away" from the beads by the high gas stream or else partially evaporated.

On the RP-C18 material, the nonpolar ethyl oleate is physisorbed. The 5 μm material has a significantly greater surface area than the glass beads, so that the trap capacity is also higher. Using this trap a quantitative recovery of 98% is achieved.

The traps containing solvent (10 ml of n-heptane in the collecting vessel) are cooled in an ice bath to 0° C. To prevent losses by evaporation of the n-heptane while the gas stream is being passed through, n-heptane is added by an external pump. The n-heptane is introduced directly in this case at the outlet of the nozzle and flows through the capillary into the collecting vessel. The flow rate is chosen so that roughly the amount of n-heptane which evaporates per unit time is compensated for. At the left trap, the gas stream escapes after it has passed through the collecting vessel, through small channels in the flask stopper (50 ml volumetric flask). Using this arrangement, only 35% of the 18:1-EE is recovered. This can be explained firstly by the evaporation of the solvent, since to maintain the level in the collecting vessel this requires a feed of about 0.5 ml/min of n-heptane. Secondly, losses due to very fine droplets (aerosol) which escape through the channels together with the gas stream cannot be prevented by this method.

For these reasons, this method was modified which is shown in the right-hand diagram. A critical factor in this case is cooling the gas stream in a long coil, after it has passed through the collecting vessel. There, in the long coil, n-heptane and sample droplets can be precipitated and, after the extraction, can be rinsed back into the collecting vessel from the top using solvent. By this means an increase in the recovery rate to 80% is achieved.

In summary it may be stated that the trap method using RP-C18 material is particularly suitable for quantitative recovery. This is employed below for all further optimization studies. It may also be converted to a larger scale, if the amount of sorbent is increased. A disadvantage is the separate rinse step. On the preparative industrial scale, cyclone separators can be used which collect pure product, without employing solvent.

Example 8

Sample Preparation

"Sample preparation" in this context includes various possibilities as to how and where the sample is added to the system.

The model substance triolein is liquid at room temperature. The reactor is filled to ⅘ with catalyst. Triolein is then weighed directly onto the catalyst. The reactor is then filled with catalyst. The sample is thus in direct contact with the catalyst and is surrounded by it. The direction of the fluid stream is chosen so that ⅘ of the catalyst are available as "reaction section", that is to say extraction is performed from the end where the sample was applied through the reactor. This method is employed for all optimization work using triolein.

In contrast, solid samples are weighed together with the catalyst and triturated in the mortar, in order to prepare a contact area as large as possible.

The effect of the amount of catalyst in relation to the sample in the reaction space; the following equation applies $$KV = \frac{\text{Total amount of catalyst}}{\text{Amount of triolein}}$$

In this case acidic aluminum oxide of activity state Super I (name: Alox A Si) was used with the following initial weights:

| Packing in this sequence | Catalyst full | Catalyst + sea sand |
|---|---|---|
| Sea sand | — | 8.5386 g |
| Alox A Si | 6.0840 g | 1.4024 g |
| Triolein | 0.0394 g | 0.0538 g |
| Alox A Si | 0.9329 g | 0.2974 g |
| KV | 178 | 31.6 |

In the case of a packing with pure sea sand, even after three minutes (first extraction step), the ethyl ester is virtually quantitatively extracted. For pure aluminum oxide, some 18:1-EE is not found until after nine minutes, and the maximum extractable amount is only 35% of that used. If the amount of aluminum oxide, based on the ethyl ester, is decreased by partial packing of the reactor with sea sand, onto which 18:1-EE is applied, significantly more ethyl ester, at 63%, is recovered.

These results permit the conclusion that some of the 18:1-EE on the aluminum oxide is irreversibly adsorbed or decomposed under the given extraction conditions. That is to say on the surface of the aluminum oxide, there are particularly reactive centers which must first be saturated before the ethyl ester can pass through. This explains the loss and the delayed extraction.

To deactivate these active centers on the surface of the aluminum oxide, the catalyst (acidic aluminum oxide, activity state Super ICN) was precoated by adding ethanol at 1.5% by weight.

Example 9

Modifier Content

Figure 3:
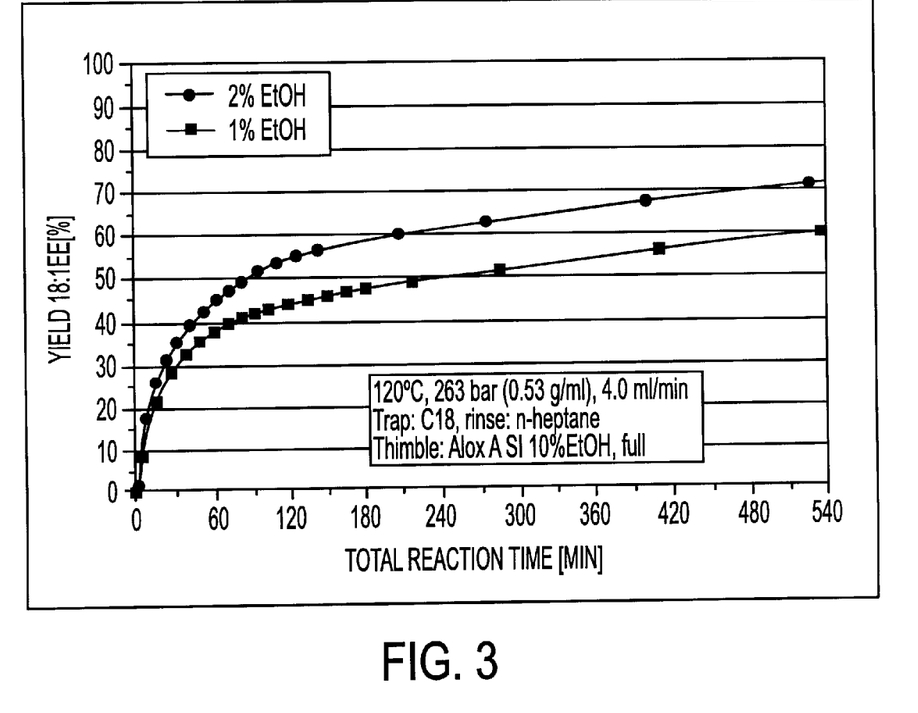

The modifier content affects firstly the extraction and secondly the reaction. For the latter, the higher the proportion of the reaction partner ethanol, the higher the reaction yield that can be achieved. On the other hand, it must be noted that with increasing modifier content, the extraction yield increases not only for 18:1-EE, but also for the starting material triolein. Therefore, the ethanol addition in the fluid must be optimized in addition to the precoating of the catalyst with ethanol. FIG. 3 shows SF-REC for triolein under identical conditions, with, in the first case 1%, and in the second case 2%, of ethanol added as modifier. For the higher ethanol content, a more rapid reaction and higher yield are found. However, increasing the ethanol content faces limits due to the simultaneously increased extraction of the triolein. The starting material must be prevented from being removed before it can react.

Example 10

Pressure/Temperature—Density

Figure 4:
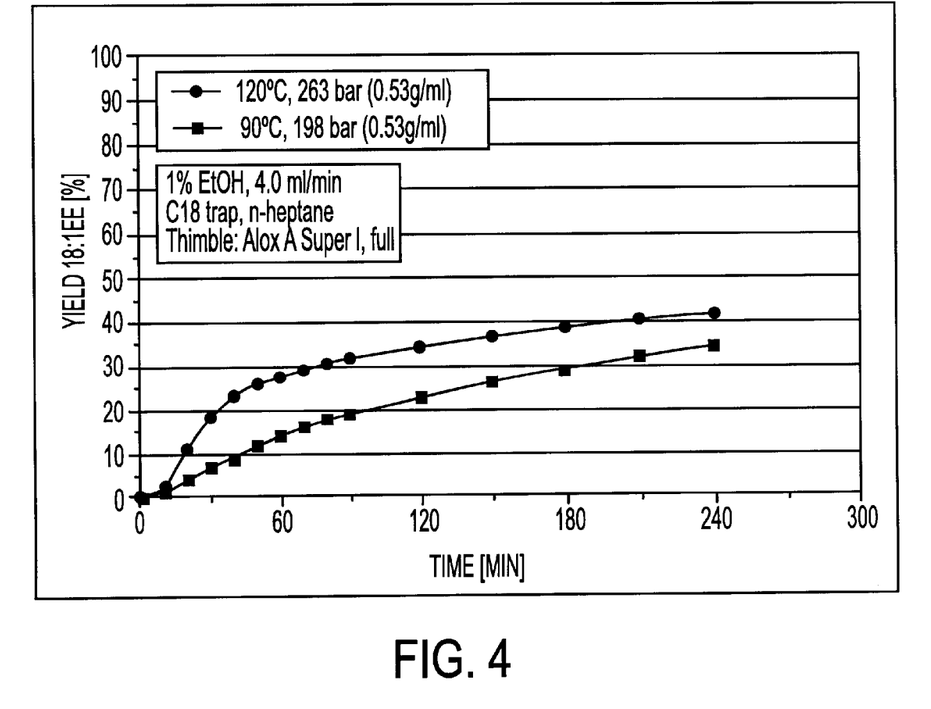

Via the pressure and temperature of the fluid, its density and thus its solvent power can be established. This is critical for the extraction yield. With it, the selectivity of the extraction can be controlled between the product ethyl ester and the starting material triglyceride. As shown in the preceding chapter, the modifier content also affects this selectivity. Overall, therefore, the SF-REC condition must be chosen so that with the highest possible modifier content, the density is so low that only the ethyl ester is selectively extracted from the reaction space. The temperature, however, as does the ethanol content, also has an effect on the reaction rate. If the reaction temperature is increased at the same density, the yield per unit time increases, as shown in FIG. 4:

In principle, the temperature can be increased with the given system up to 150° C. However, the risk of isomerization or decomposition of the unsaturated fatty acids also increases with it. Up to a temperature of 140° C., no losses have been established to date for 18:1-EE, which is of relevance to the yield.

Overall, the picture of parameters with effects which result from the experiments which have been carried out are as follows.

Temperature and modifier content have a direct effect on the reaction yield, that is to say the conversion rate of the transesterification. They should both be as high as possible to achieve a rapid reaction. However, the extraction of the product from the reaction space should proceed as selectively as possible compared with the starting material, that is to say the solvent power of the fluid must be sufficient to achieve as complete as possible an extraction of the ethyl ester but as low as possible an extraction of the triglyceride. Therefore, the following strategy was used for optimization: by lowering the pressure, with simultaneous increase in temperature and modifier content, the extraction can be sufficiently selective, but the conversion rate appropriately high. The optimized conditions are specified below:

Example 11

Optimized SF-REC

The optimum SF-REC conditions are given from the previous examples as follows:

System: HEWLETT-PACKARD SFE Module 7680T
Pressure: 254 bar
Temperature: 140° C.
Density: 0.45 g/ml
Modifier: 5% EtOH
Flow rate: 4.0 ml/min
Catalyst: acidic aluminum oxide activity state Super I (ICN)+15% ethanol
Reactor: completely filled with catalyst (7.1 g)
Sample: Triolein 54.1 mg (FLUKA 97%)
Trap method: Merck RP-C18 material 5 μm
Rinse step: 1.3 ml of n-heptane each time
Nozzle temperature during extraction: 90° C.
Trap temperature during extraction: 85° C.
Nozzle temperature for the rinse step: 70° C.
Trap temperature for the rinse step: 60° C.

Figure 5:
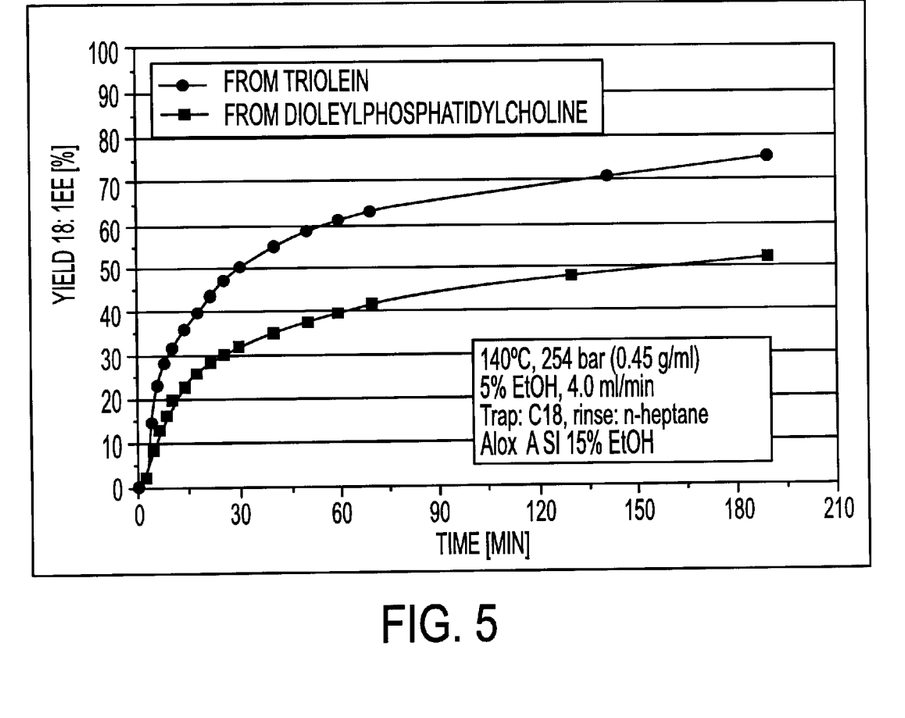

This gives the following kinetics for converting the triolein to 18:1-EE and for extracting the starting material (FIG. 5).

At the end of the measurement (730 minutes of total reaction time), in total, 93% ethyl ester has been taken off from the system, which corresponds to a virtually quantitative conversion. If the amount of co-extracted triolein is added to this, a total recovery rate of 96% is achieved, which, considering the long time period, can be considered to be quantitative.

If the course of the kinetics is considered, it appears that the reaction proceeds very rapidly at the start, becoming slower and slower toward the end. This may be simply explained by a 1st order time law. Since the amount of unreacted triolein constantly becomes less, less ethyl ester is also formed in absolute terms.

Example 12

Application of SF-REC to Lecithin

The second model substance chosen was a lecithin having two oleic acids, dioleylphosphatidylcholine. This was reacted under the conditions optimized for triolein. The reaction kinetics may be seen in FIG. 5:

If the kinetics are compared with those for the transesterification of triolein, it is observed that the reaction proceeds slower for the phospholipid under the same conditions (FIG. 5).

For example, after the same time (130 minutes, total of the net extraction time), from the lecithin, just 49%, and from the triolein over 70%, of the oleic acid present therein is released as ethyl ester. The transesterification therefore proceeds with a lower yield per unit time for the phosphatide. For this lipid, however, the modifier content may be further increased, since here the starting material is significantly more polar than triolein. The conditions for the transesterification of polar lipids can be optimized according to the same aspects as for the triglycerides. Overall improved selectivity of the extraction/chromatography may be expected, since in addition to the differences in molecular mass (triolein: 885.46 g/mol—dioleylphosphatidylcholine: 786.1 g/mol—18:1-EE: 310.5 g/mol), the polarity differences between starting material and product are greater.

The use of an RP-C18 material as trap makes possible quantitative recovery of the product extracted from the reaction space.

By the interaction of density of the reaction medium, controlled via temperature and pressure, and the modifier content, the solvent power of the fluid can be set. Thus the selective extraction of the ethyl ester product can be achieved. By increasing the reaction temperature and the ethanol content, the conversion rate is increased, with at the same time the density being kept so low that the selectivity of the extraction/chromatography is maintained. The SF-REC conditions may thus be optimized so that quantitative transesterification of triolein to ethyl oleate can proceed.

With this procedure, various samples of biological origin are transesterified below in order to demonstrate the applicability to real biomatrices.

Example 13

Application to a Biological Source/Matrix: Dried Biomass of GLA Strain

Below, a freeze-dried (lyophilized) powder produced from the fermentation of microorganisms is termed dried biomass. The first dry biomass originates from a so-called GLA strain. This has a particularly high γ-linolenic acid (GLA) content, most of which is present bound in phosphatides. SF-REC was carried out under the following conditions:

| | |
|---|---|
| Flow rate: | 4.0 ml/min |
| Pressure: | 198 bar |
| Temperature: | 90° C. |
| Modifier: | 1% EtOH |
| Steps: | 2 min static |
| | 10 min dynamic |

The n-heptane solution obtained from the second step was analyzed by GC-MS to identify the ethyl esters of fatty acids present. The chromatogram and a section are shown in FIG. 6.

Figure 6:
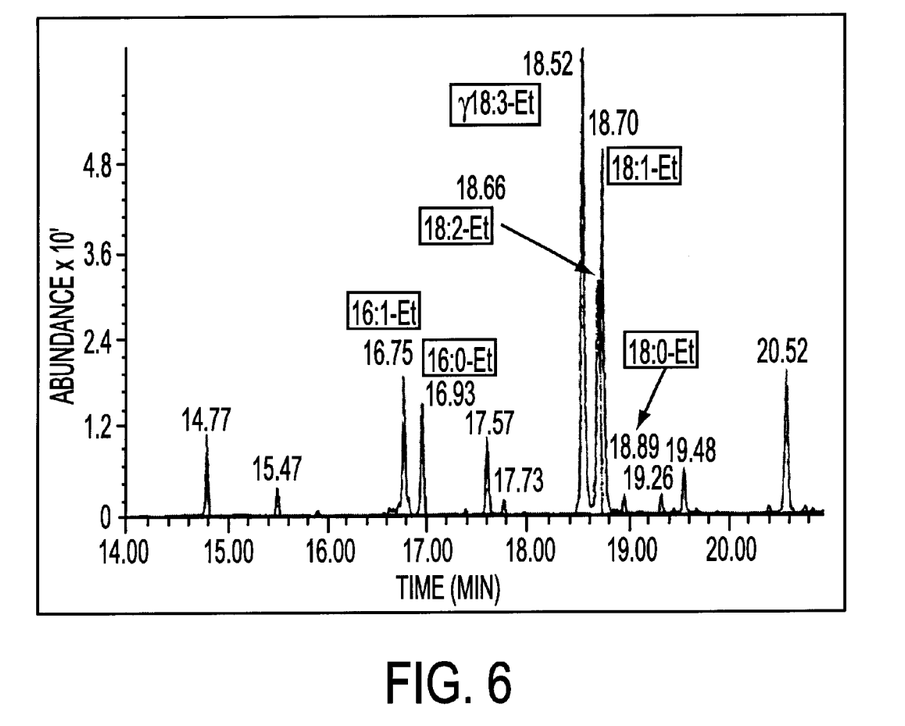

In addition to the GLA-EE, in FIG. 6 a number of other ethyl esters of fatty acid can also be seen, particularly ethyl oleate and ethyl linoleate (18:1-EE and 18:2-EE), but also C14, C16 and C20 fatty acids.

Example 14

Wet Biomass of GLA Strain

Figure 7:
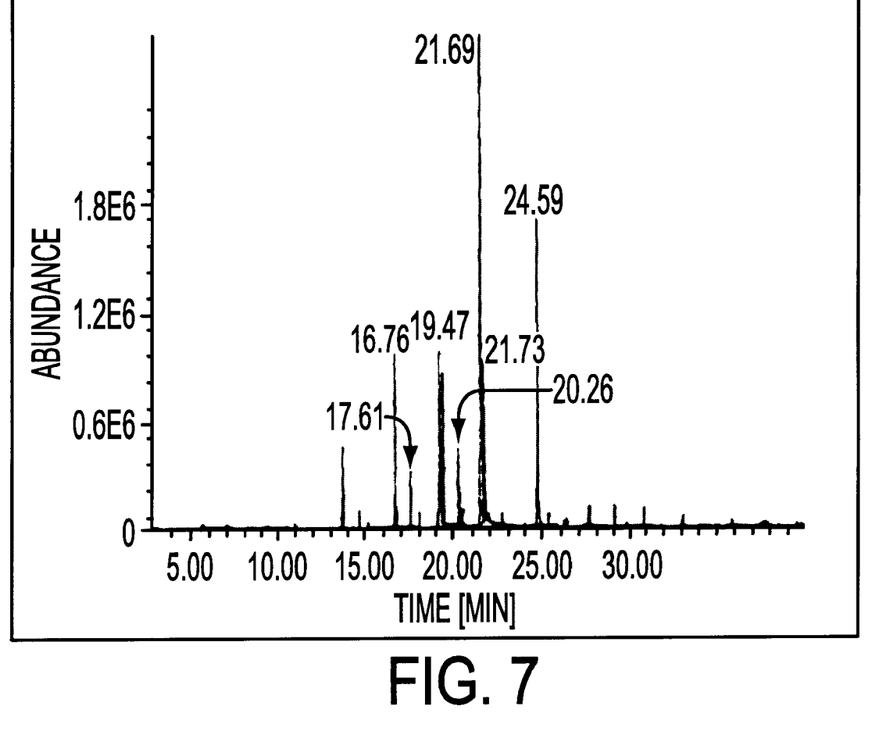

The aqueous suspension of the biomass (without lyophilization) is called wet biomass. If this is converted directly in an SF-REC, owing to the excess of water, no transesterification of the lipids to the ethyl esters takes place, but hydrolysis to the free acids takes place. This verifies the analysis by GC-MS (FIG. 7). SF-REC was carried out under the following conditions:

| | |
|---|---|
| Flow rate: | 1.0 ml/min |
| Pressure: | 198 bar (0.72 g/ml) |
| Temperature: | 60° C. |
| Modifier: | 10% EtOH |
| Steps: | 2 min static |
| | 10 min dynamic |

1.56 g of wet biomass were absorbed on 13.3 g of sea sand. Of this, 9.11 g (equivalent to 0.96 g of wet biomass) were mixed with 1.43 g of acidic aluminum oxide activity state 1. The SF-REC was carried out with 10% ethanol and a density of 0.72 g/ml, since the free acids require stronger eluting conditions than the ethyl esters in order to be removed from the reaction space.

If this is compared with the results for the dried biomass of the same GLA strain (FIG. 6), an identical fatty acid spectrum is found. With this example, the possibility in principle of a hydrolysis instead of transesterification by means of SF-REC can be demonstrated. This is also of interest with respect to cost savings, if the complex freeze-drying step can be dispensed with. However, the ethyl esters may be separated chromatographically more simply in a subsequent SFC step, as is the case for the free acids. Other optimizations of the conditions must still be carried out with respect to the yield of the SF-REC.

Example 15

Dried Biomass of DHA Strain

The lyophilized biomass of the DHA strain contains, in addition to docosahexaenoic acid (DHA 22:6) especially docosapentaenoic acid (DPA 22:5). The total lipid content of the dried biomass is about 40% by weight. In turn, 40% of the fatty acids therein is DHA. The lipid content is present virtually exclusively in the form of triglycerides.

The dried biomass was triturated in a mortar with ten times the amount of acidic aluminum oxide activity Super I, which was coated with 15% ethanol, and packed into the reactor. SF-REC was carried out under the following conditions:

Flow rate: 4.0 ml/min
Pressure: 263 bar
Temperature: 120° C.
Modifier: 3% EtOH

Figure 8:
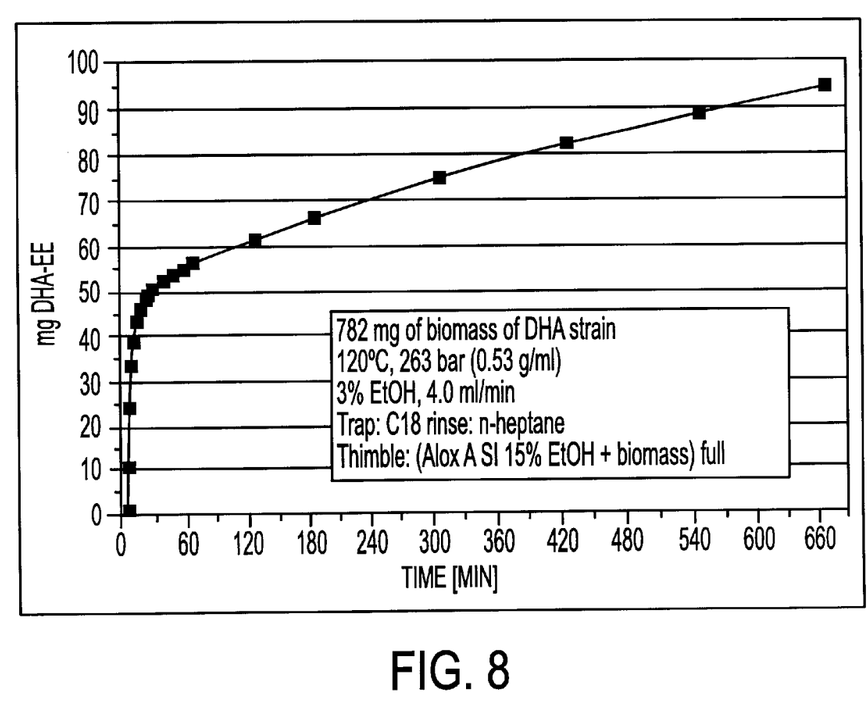
Figure 9:
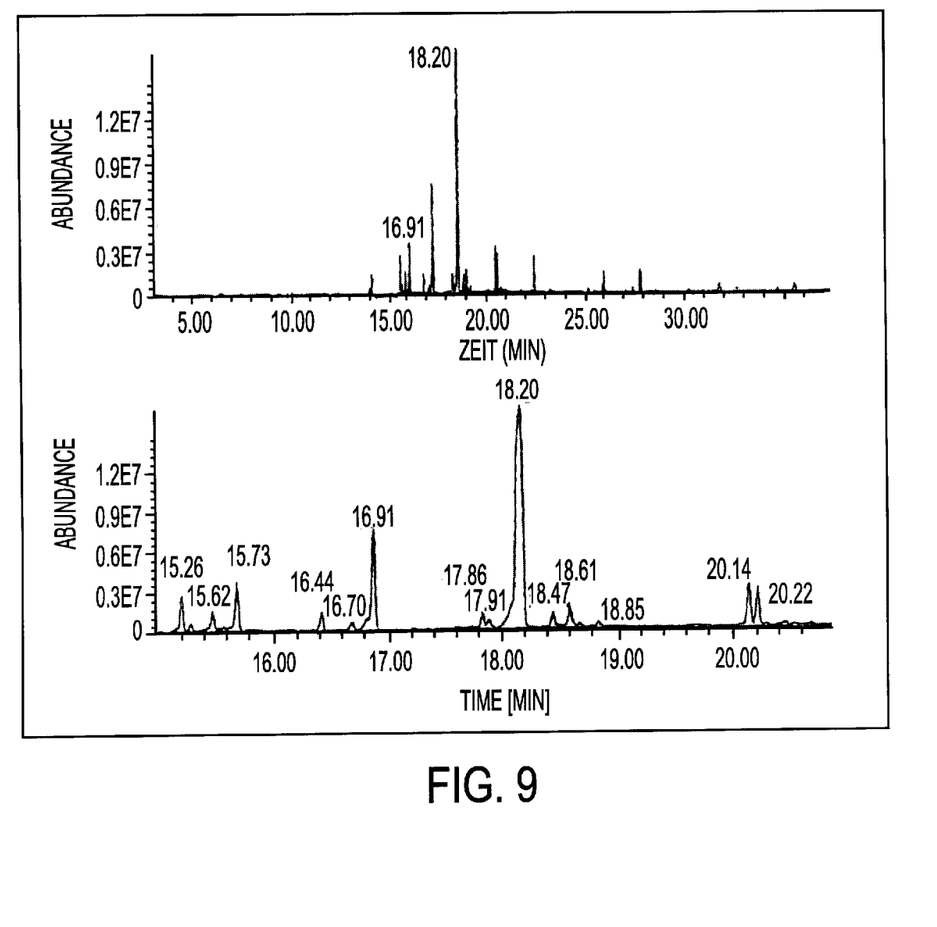
Figure 10:
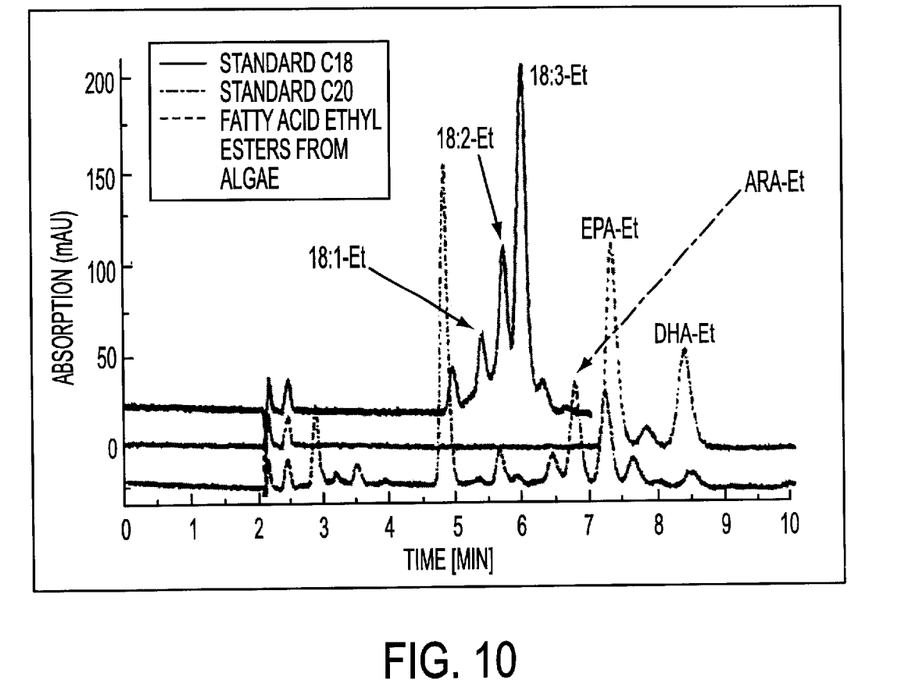

The reaction kinetics are shown in FIG. 8.

The amount of DHA-EE was determined using a DHA standard (90%, KD-PHARMA, Bexbach).

If it is assumed that 40% by weight of lipids are present in the biomass and of this, in turn 40% comprise DHA, in theory, about 125 mg of DHA are produced by 782 mg of biomass. This is equivalent to 135 mg of DHA-EE. After 670 minutes of net extraction time, approximately 95 mg of DHA-EE were found. This gives a conversion rate of 70% for this actual sample. Under similar conditions (2% ethanol and Alox 10%: FIG. 5), for the model substance triolein, after the same time, a yield of 77% was achieved. Thus there is virtually no impairment of the conversion by the same matrix.

The applicability of SF-REC to real samples was demonstrated. For the so-called GLA strain, which principally comprises γ-linolenic acid, both the lyophilized biomass and also an aqueous suspension of the biomass could be reacted. In the first case, in a transesterification reaction with ethanol the ethyl esters are formed, in the second case, by hydrolysis, the free acids are formed.

From the dried biomass of the DHA strain, which contains especially docosahexaenoic and docosapentaenoic acids, the fatty acids could also be obtained as ethyl esters by SF-REC.

Example 16

Use of SF-REC—Production of Valuable Biogenic Substances from Algae

The purpose of the experiments carried out here is to test the possibility of producing valuable substances from algae by means of various extraction methods. A key role here is played in particular by polyunsaturated fatty acids which are present in algae in rather high concentrations. Those which may be mentioned here are in particular arachidonic acid (5,8,11,14-eicosatetraenoic acid; ARA) and eicosapentaenoic acid (EPA).

In addition, unsaturated fatty acids having 18 carbon atoms, such as gamma-linolenic acid (GLA) are also of particular importance.

In addition to these substances, in algae, depending on the strain, a number of pigments, such as chlorophyll, xanthophylls (carotenoids), but also other specific substances, such as the phycobiliprotein class are found. In red algae (Rhodophytha), phycoerythrins, in particular are found. Below, the way in which these different substance classes can be produced in pure form from the algal material is to be shown. In particular in this case the fact must be noted that the said substance classes differ in their polarity. Thus stepwise extraction with media of different polarity suggests itself, in order to achieve prepurification and separation.

Example 17

Extraction with Supercritical Carbon Dioxide (SFE)

SFE with pure $CO_2$ is the first step in the production of the fatty acids from algae. More polar compounds can then be extracted in the second step by using ethanol as modifier. An extraction of polar compounds, in particular those which show good water solubility, cannot be achieved by $CO_2$, so that these can then be extracted with water in a third step.

Example 18

Extraction with Pure Carbon Dioxide

About 2 grams of the dried algae are triturated with about 5 grams of sea sand in a mortar and packed into an extraction thimble. Extraction is performed under various conditions for 60 minutes in each case at 4.0 ml/min flow rate and the extracted substances are deposited in a trap (glass beads) after depressurizing the $CO_2$ to atmospheric pressure. From this trap they are then eluted with n-heptane after each extraction step.

The first extraction was carried out at a relatively low $CO_2$ density: 204 bar, 60° C. (density: 0.73 g/ml). A dark-yellow to green solution is obtained which has a red fluorescence (excitation wavelength: 366 nm), so that it may be assumed that even chlorophyll is extracted under these conditions. This does not only interfere with determining the fatty acids, but also represents an unwanted impurity.

Example 19

Extraction with Modifier

With increasing pressure and also by using 10% ethanol as modifier, after several hours of extraction, the chlorophyll can be removed from the algal material virtually completely.

Example 20

Extraction in the Presence of an Adsorbent/In-situ Transesterification by SF-REC To avoid the unwanted extraction of chlorophyll in the first fraction, the algae were then triturated with an adsorbent (aluminum oxide) instead of sea sand and extracted under the same conditions as above. It is found that the fractions which were obtained without modifier are not green, but only slightly yellow.

Extraction under 204 bar, 60° C., 1% ethanol in the presence of acidic aluminum oxide produces a yellow solution which has a bluish fluorescence (366 nm). The cause of the coloration is apparently to be found in xanthophylls here, which are yellow, nonpolar plant pigments. A more precise investigation is still required for an exact determination.

The in-situ transesterification of the lipids takes place in the presence of acidic aluminum oxide, which transesterification firstly makes accessible the fatty acid spectrum of the algae, and secondly also demonstrates as a model the use of preparative production of the ethyl esters of fatty acid from a biological matrix. Analysis of the product produced by GC-MS may be seen below (FIG. 8).

The UV spectrum up to 600 nm chlorophyll was recorded using a diode array detector. The yellow fraction therefore does not contain chlorophyll. Identification of the peak at 3.1 min as yellow pigments was made by moving a thin-layer chromatography plate past the SFC outlet at a defined speed. On the plate, under UV light, a bluish-fluorescing spot at 3.1 min could be seen.

Therefore, it is possible to transesterify the valuable fatty acids from the algae in situ and to isolate them as ethyl esters, without co-extracting chlorophyll.

Example 21

Extraction with Ethanol

The direct extraction of the algae with ethanol produces green solutions. Chlorophyll can therefore be removed from the algae with ethanol.

After SFE for several hours with 10% ethanol as modifier, the algae were substantially freed from chlorophyll. Subsequent direct extraction with ethanol shows only weakly green solutions. The red pigment of the algae does not dissolve in ethanol, so that separation from chlorophyll is possible either with SFE and ethanol or directly with ethanol.

Example 22

Extraction with Water

A purple solution can be obtained with water, both from the algae which have already been "prepurified" with SFE, and from the untreated algae. This solution shows orange fluorescence under excitation with UV light (366 nm). The purple pigment can thus be prepared in an aqueous step separately from the fats and chlorophyll.

The aluminum oxide initially used can be removed from the algal residues by sedimentation in water. It shows a mint-green color, which is concluded to be due to adsorbed chlorophyll.

Example 23

UV/VIS Spectra of the Resultant Solutions

The following are used to characterize the three fractions:

(1) Yellow solution in n-heptane—blue to green fluorescence:
SFE/SFR 204 bar, 60° C., 1% ethanol in the presence of acidic aluminum oxide
(2) Deep-green solution in n-heptane—red fluorescence:
SFE 204 bar, 60° C., 10% ethanol in the presence of aluminum oxide
(3) Purple solution in water—orange fluorescence:
aqueous extraction of the SFE residue, centrifuge.

The color of the yellow solution may be explained in the spectrum by the flank which extends from the UV region to 500 nm. An absorption maximum may be seen in the UV region at 282.4 nm. The reason for the green color of the chlorophyll solution is the absorption maximum at 662.6 nm. Numerous maxima of relatively low height may be found in the region of visible light. The highest maximum is at 410 nm. The purple solution has the greatest absorption in the visible region at 545.5 nm (the algal pigment β-phycoerythrin, according to literature data, has an absorption maximum at 546 nm). In the UV region, a maximum is found at 272.2 nm, which may be due to light scattering by the slightly turbid solution.

The examples show that extraction and separation of the desired substances is possible, for example, from the given algae.

By means of the inventive method with 1% ethanol as modifier in the presence of acidic aluminum oxide as adsorbent and as catalyst, the valuable polyunsaturated fatty acids can be obtained as ethyl esters. They are extracted together with yellow pigments, these probably being xanthophylls. These can be removed in a further work up step, for example using preparative SFC.

In a second step, the interfering chlorophyll can be removed from the matrix either by SFE with more than 10% ethanol as modifier and higher pressure (higher density) or by direct extraction with ethanol. In this case the purple pigment of algae is not extracted.

This can be extracted with water either directly from the algae or after the first two steps.

The advantages of the methods used are that any contact with toxic solvents may be avoided, so that the substances obtained are available for pharmaceutical or food use.

Conversion of the triglyceride triolein to ethyl oleate served as model example for transesterification with ethanol on acidic aluminum oxide. SF-REC was optimized for this example with respect to equipment conditions and process sequence. A virtually quantitative transesterification with 93% yield was achieved.

SF-REC could also be carried out for the model phosphatide substance dioleylphosphatidylcholine.

As real samples, a plurality of freeze-dried fermentation products (dried biomasses) were available which had a high content of PUFAs. These were converted directly in an SF-REC. Application of the method to an undried fermentation product (wet biomass) led, owing to the excess water, to hydrolysis, so that in this case the free fatty acids were produced.

The application to dried red algae also demonstrates the applicability of SF-REC to this type of samples.

What is claimed is:

1. A method for the preparation and selective isolation of fatty esters and/or fatty acids from a biological source comprising the steps of:
(a) reacting said biological source with an inert catalyst using continuous in-situ extraction, reaction chromatography in the presence of a compressed gas stream and 0.5 to 5% volume of C1–C5 alcohol modifier;
(b) subjecting said inert catalyst to said chromatography, wherein said inert catalyst has chromatographic retention and exclusively desorbs and elutes the reaction products; and
(c) extracting said fatty esters or fatty acids from said desorbed and eluted reaction products.

2. The method as claimed in claim 1, wherein the catalyst is mixed with the biological source.

3. The method as claimed in claim 1, wherein the inert catalyst is produced from aluminum oxide and/or silica gel and if appropriate other additives and aids.

4. The method as claimed in claim 1, wherein the modifier is ethanol, preferably 1% by volume in the compressed gas.

5. The method as claimed in claim 1, wherein the compressed gas is carbon dioxide.

6. The method as claimed in claim 1, wherein the starting materials are completely converted to the reaction products.

7. The method as claimed in claim 1, wherein the reaction products are obtainable from biological sources.

8. The method as claimed in claim 7, wherein said biological sources comprise a biological source selected from the group consisting of microalgae, protozoa, fungi and bacteria.

9. The method as claimed in claim 1, wherein said reacting step, said subjecting step and said extracting step are performed simultaneously.

* * * * *